United States Patent [19]

Van Moerkerken

[11] Patent Number: 5,626,831

[45] Date of Patent: May 6, 1997

[54] METHOD FOR RELIEF AND PREVENTION OF COMMON COLD, AND COMPOSITIONS

[76] Inventor: Arthur Van Moerkerken, 18761 W. Dixie Hwy., #209, North Miami Beach, Fla. 33180

[21] Appl. No.: 575,858

[22] Filed: Dec. 20, 1995

[51] Int. Cl.$^6$ .............................. A61K 49/00; G01N 31/00; G01N 33/48
[52] U.S. Cl. ............................................................. 424/9.2
[58] Field of Search ................................. 424/1.11, 1.65, 424/9.1, 9.2, 400, 439, 451, 456, 463, 464, 474

[56] References Cited

U.S. PATENT DOCUMENTS

| Re. 33,465 | 11/1990 | Eby, III | 424/400 |
|---|---|---|---|
| 5,112,617 | 5/1992 | Criscudo et al. | 424/400 |
| 5,240,694 | 8/1993 | Gwaltney, Jr. | 424/400 |
| 5,286,748 | 2/1994 | Eby, III | 424/400 |
| 5,409,905 | 4/1995 | Eby, III | 424/400 |
| 5,492,689 | 2/1996 | Gwatney, Jr. | 424/400 |

FOREIGN PATENT DOCUMENTS

| 9204022 | 3/1992 | WIPO . |
|---|---|---|
| 9204021 | 3/1992 | WIPO . |
| 9408551 | 4/1994 | WIPO . |
| 9425009 | 11/1994 | WIPO . |
| 9507103 | 3/1995 | WIPO . |

*Primary Examiner*—John Kight
*Assistant Examiner*—Dameron L. Jones
*Attorney, Agent, or Firm*—Otto S. Kauder

[57] ABSTRACT

Disclosed is the method of determining the effectiveness of an agent for relieving symptoms of the common cold, comprising the steps of a) exposing a susceptible subject to vapors of a trigger substance reproducibly effective in producing within a period of 30 minutes a running nose lasting for at least 6 hours in the absence of treatment, b) administering to said subject having been exposed to a trigger substance a predetermined quantity of the agent whose effectiveness is to be determined, c) measuring the time required for the running nose to be abated, and d) comparing the time required for the running nose to be abated with and without the administration of said agent.

Also disclosed are effective quantities of certain nutrient substances which can reproducibly relieve symptoms of the common cold produced in a susceptible subject by the administration of a trigger substance.

35 Claims, No Drawings

METHOD FOR RELIEF AND PREVENTION OF COMMON COLD, AND COMPOSITIONS

This invention relates to the relief and prevention of the so-called common cold, also known as upper respiratory infection and as acute coryza. More particularly, this invention relates to the avoidance or at least mitigation of a tendency in some individuals to develop the symptoms of nasal or throat discomfort, followed by sneezing, rhinorrhea (running nose), and malaise.(see Merck Manual, 16th edition, 1992, pages 190–192). As stated in this reference work, "Many viruses cause the common cold, including those in the picornavirus (rhinovirus, certain echoviruses, and coxsackieviruses), influenza, parainfluenza, respiratory syncytial, coronavirus, and adenovirus groups. Most colds (30–50%) are caused by one of the >100 serotypes of the rhinovirus group. Pinpointing the specific cause of each illness by virus isolation or serologic tests is impractical ... Predisposing factors have not been clearly identified. Chilling the body surface does not by itself induce colds, and an individual's susceptibility is not affected by either health and nutritional status or upper respiratory tract abnormalities (e.g. enlarged tonsils or adenoids). Infection may be facilitated by excessive fatigue, emotional distress, or allergic nasopharyngeal disorders and during the midphase of the menstrual cycle. However, the most important determinant of infection is the presence of specific neutralizing antibody, which indicates previous exposure to a virus and offers relative protection.

Thus the sufferer is told that the condition may have any of a number of possible causes, and the clinical symptoms and signs are non-specific. The condition is stated to be widespread and, when no complications occur, symptoms normally resolve in 4 to 10 days. Also according to the Merck Manual, "Many means of preventing acquisition and spread of common colds have been tried, including polyvalent bacterial vaccines, alkalis, citrus fruits, vitamins, ultraviolet lights, and glycol aerosols, but none has been effective. In controlled trials, large (as much as 2 grams per day) prophylactic oral doses of vitamin C have not altered the frequency of acquisition of rhinovirus common colds or the amount of virus shedding. However, some studies have shown a reduction in duration of disability among persons who took as much as 8 g/day on the first day of disease, although no reduction inn virus shedding has been noted."

Remarkably, the only treatments recommended by this reference are a warm, comfortable enronment and measures to prevent direct spread of infection for all patients, rest at home for those with fever or acute symptoms of infection, and steam inhalation to mobilize secretions and help relieve chest tightness. Many other treatments including antipyretics and analgesics such as aspirin, antihistamines, and antibiotics, are listed but also deprecated as being of little benefit and/or subject to various drawbacks.

Kagitani et al U.S. Pat. No. 4,265,888 discloses a pharmaceutical composition comprising an injection powder preparation of an acetylsalicylate (aspirin salt) obtained by reacting acetylsalicylic acid and a basic amino acid and incorporated with 1% w/w or more of calcium chloride. The preferred basic amino acid is DL-lysine. In DL-lysine acetylsalicylate, both reactants are combined in a molar ratio of 1:1. In using the preparation, it is dissolved in distilled water for injection. The diseases for which the preparation is efficacious include post-operational pain and other pains for which oral administration of an analgesic is effective; rheumatoid diseases (especially efficacious for progressive rheumatoid), neuralgia and neuritis; and hyperthermia (common cold, bronchitis, and other central fever). In this disclosure, the active agent is clearly the acetylsalicylate and the basic amino acid and calcium chloride act to solubilize and stabilize the preparation for injection use.

J. C. Godfrey U.S. Pat. No. 4,684,528 discloses that compositions containing a zinc compound such as zinc gluconate, a base material such as a candy or syrup and certain amino acids in which the molecular ratio of amino acid to zinc is in the range of two two twenty are very pleasant to the taste and leave no undesirable aftertaste. The amino acids found useful for this purpose are glycine, L-alanine, D,L-alanine, L-2-aminobutyric acid, D,L-2-aminobutyric acid, L-valine, D,L-valine, L-isovaline, D,L-isovaline, L-leucine, D,L-leucine, D-isoleucine, D,L-isoleucine, L-lysine, and D,L-lysine. It is also disclosed that certain other amino acids such as aspartic and glutamic acids are not useful for this purpose. Therefore, it has been found that it is not possible to predict which zinc and amino acid combination will have an acceptable taste unless it is prepared and tested. Furthermore, the zinc supplement compositions which include the select amino acid possess in general very pleasant flavors. This permits the formulation of compositions which will release over an extended period of time substantial amounts of zinc ions locally in the mouth or in the mouth and throat as necessary for certain applications, including the control of the common cold.

J. C. Godfrey U.S. Pat. No. 5,250,569 discloses compositions for use in treatments to relieve upper respiratory discomfort containing an aluminum compound, a base material such as a candy or syrup and certain amino acids in which the molecular ratio of amine acid to aluminum is in the range of two two twenty are very pleasant to the taste and leave no undesirable aftertaste. The amino acids found useful for this purpose are glycine, L-alanine, D,L-alanine, L-2-aminobutyric acid, D,L-2-aminobutyric acid, L-valine, D,L-valine:, L-isovaline, D,L-isovaline, L-leucine, D,L-leucine, D-isoleucine, D,l.-isoleucine, L-lysine, and D,L-lysine. It is also disclosed that certain other amino acids such as aspartic and glutamic acids are not useful for this purpose. Therefore, it has been found that lit is not possible to predict which aluminum and amino acid combination will have an acceptable taste unless it is prepared and tested. The aluminum compounds which can be used in combination with the amino acids noted above can be any of the forms commonly used such as the sulfate, chloride hexahydrate, acetate, acetotartrate, ammonium sulfate, diacetate, hydroxychloride, magnesium silicate, potassium sulfate, sodium sulfate, acetate oxide, gluconate, gluc, uronate, and ascorbate, as well as complexes of trivalent aluminum with the amino acids.

J. M. Gwaltney Jr. U.S. Pat. No. 5,422,097 discloses a method to treat the common cold which utilizes both antiviral and antiinflammatory compounds and employs the simultaneous administration of intranasal and oral medicaments. Also disclosed are investigations in which human volunteers were subjected to a virus challenge with intranasally administered Hank's strain of rhinovirus. Antiviral agents disclosed include interferon a-2 and others itemized at column 9 line 61 to column 10 line 40. Antiinflammatory agents disclosed include iprotrophen, naproxen, phenylephrine, chlorpheniramine, and others itemized at column 10 lines 41–64.

However, there is as yet no evidence that any of the above proposed treatments have succeeded in reliably controlling the so-called common cold.

Against this background, there clearly exists a need for improved oral remedies and preventive methods for relieving and preventing the so-called common cold, as well as improved methods for discovering such improved remedies and preventive methods.

SUMMARY OF THE INVENTION

In accordance with this invention, I have found that I can reproducibly cause a susceptible human subject to experience a reproducible appearance of a running nose condition symptomatic of the common cold within a short period of time upon exposure to vapors of any of a class of substances which I propose to call trigger substances. These trigger substances are found in products used in a large number of households and in the quantities needed as trigger substances in accordance with this invention are without effect on the great majority of the human population. In a susceptible subject, however, the observed trigger effect is both reproducible and sufficiently long lasting to serve as research tool for the evaluation of agents effective in remedying or preventing the appearance of a running nose condition as in the common cold. Accordingly, the method of determining the effectiveness of an agent for remedying or preventing symptoms of the common cold comprises the steps of a) exposing a susceptible subject to vapors of a trigger substance reproducibly effective in producing within a period of 30 minutes a running nose lasting for at least 6 hours in the absence of treatment, b) administering to said subject having been exposed to a trigger substance a predetermined quantity of the agent whose effectiveness is to be determined, c) measuring the time required for the running nose to be abated, and d) comparing the time required for the running nose to be abated with and without the administration of said agent.

Also in accordance with this invention, I have found that effective quantities of certain nutrient substances can reproducibly prevent appearance of symptoms of the common cold such as running nose in a susceptible subject when given prior to exposure to a trigger substance and relieve such symptoms when given after such exposure. Being nutrient substances that are ingested and metabolized by humans daily, such substances are inherently safe. Accordingly, the method of preventing or relieving the appearance of common cold symptoms in a person in need of such relief, comprises the administration to such person of a quantity of an agent determined to be effective in preventing the appearance of a running nose condition in a susceptible subject following exposure to a trigger substance.

Also in accordance with this invention, I have found that an agent found effective in accordance with this invention in preventing the appearance of common cold symptoms such as running nose can be combined with a pharmaceutically acceptable carrier to provide an effective palatable common cold prophylactic or remedy composition. Moreover, I have found that a combination of two or more selected agents found effective in accordance with this invention in preventing the appearance of common cold symptoms such as running nose can be combined with a pharmaceutically acceptable carrier to provide a pleasant tasting as well as effective and palatable common cold preventing remedy composition.

DESCRIPTION OF PREFERRED EMBODIMENTS

Trigger Substances

A trigger substance according to this invention is defined as any substance that, when exposed in the form of a vapor to a susceptible human subject, reproducibly gives rise to a running nose condition in such subject in a time period of thirty minutes or less. Preferred trigger substances are those whose vapors are known to be safe to expose to a human subject in the amounts needed, particularly substances known to be present in products sold in retail establishments for household use or authoritatively regulated for such use under observance of appropriate limitations. Included among such trigger substances are basic nitrogen compounds such as alkanolamines and especially ammonia as found in aqueous ammonia solutions, formulated liquid household cleaning products, hair waving preparations, and the like. An immediate effect of such basic nitrogen compounds in triggering symptoms of the common cold such as running nose within thirty minutes or less has not previously been reported.

The quantity of trigger substance to be exposed to a susceptible person for appearance of cold symptoms to be reproducible is readily determined empirically. For example, a reproducible appearance of a running nose condition within thirty minutes or less has been noted by a susceptible individual upon exposure within 4 feet of a 40 milliliter sample of household ammonia for less than five minutes.

Agents effective in preventing appearance of cold symptoms

In accordance with this invention, any desired agent can be tested for its effectiveness in preventing the appearance of cold symptoms otherwise produced in a susceptible individual by exposure to a trigger substance. The only limitation is the practical requirement of not doing harm to such individual. For that reason, I have sought effective agents principally among substances known to be safe to administer to a human subject, particularly substances known to be nutrients ingested and metabolized by human beings on a daily or at least frequent basis. I have tested many nutrient substances and found effective among these a restricted group of water soluble aminocarboxylic acid compounds at dose levels in the range from 200 to 20000 milligrams. I use the term water soluble to refer to a solubility of at least three grams in 100 ml of water at 25° C.

A preferred group of water soluble aminocarboxylic acid compounds effective according to this invention in preventing appearance of cold symptoms can be represented by formula (I):

$$X—(CH_2)_n—CH(O)_qH—CH—COO^- \atop | \atop (NH_2^+)_pH \qquad (I)$$

in which X is selected from the group consisting of —SH, —CONH$_2$,

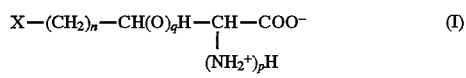

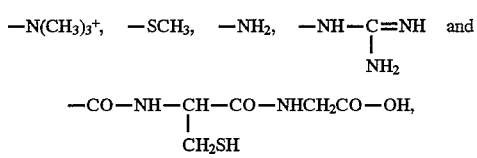

n is zero, one, or two, and p and q are each zero or one, provided that p and q are not both zero and p is zero and q is one only when X is —N(CH$_3$)$_3$+.

Table 1 which follows includes particularly preferred water soluble aminocarboxylic acid compounds represented by formula (I) which I have found effective in preventing appearance of cold symptoms when administered before exposure to a trigger substance.

companion substances to effective agents according to this invention. In this way such substances can contribute to the useful properties of the effective agents by enhancing their speed of action, palatability and/or taste characteristics. When present as companion substances to effective agents their concentration will typically range from 1 to 10 weight percent of the effective agent.

TABLE 1

| # | Name | X | n | p | q |
|---|------|---|---|---|---|
| 1 | 2-amino-3-mercapto-propanoic acid | —SH | 0 | 1 | 0 |
| 2 | 2-amino-4-carbamoyl-butanoic acid | —CONH$_2$ | 1 | 1 | 0 |
| 3 | 2-amino-4-methylthio-butanoic acid | —SCH$_3$ | 1 | 1 | 0 |
| 4 | 2,5-diaminopentanoic acid | —NH$_2$ | 2 | 1 | 0 |
| 5 | 2-amino-5-guanido-pentanoic acid | —NH—C(=NH)—NH$_2$ | 2 | 1 | 0 |
| 6 | 2-(4-amino-5-carboxypentan-amido)-3-mercapto-N-carboxymethylpropanoamide | —CO—NH—CH(CH$_2$SH)—CO—NHCH$_2$CO—OH | 1 | 1 | 0 |
| 7 | 3-hydroxy-4-trimethyl-ammoniobutanoate | —N(CH$_3$)$_3$+ | 1 | 0 | 1 |

Formula (I) and all the effective compounds listed in Table 1 contain an assymetric carbon atom and hence exist in non-superimposable optically active forms (so-called D and L forms) and in racemic mixtures or DL forms. Both D and L forms of the effective compounds and racemic mixtures thereof are contemplated in accordance with this invention.

There is nothing about the structures of the effective compounds of this invention or their known nutrient properties that would have enabled one to predict their effectiveness in preventing appearance of cold symptoms in accordance with this invention. This unpredictability is further underscored by the finding that a number of aminocarboxylic acid compounds structurally similar to those effective according to this invention but not structured according to formula (I) are ineffective. In Table 2 following, there are listed a number of aminocarboxylic acid compounds found ineffective in preventing appearance of cold symptoms when administered before exposure to a trigger substance. Some of these compounds can be represented by formula (II)

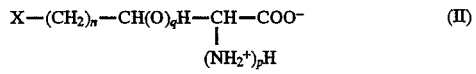

$$X—(CH_2)_n—CH(O)_qH—CH(NH_2^+)_pH—COO^- \quad (II)$$

in which the assignments of X and/or n differ from those in formula (I)

TABLE 2

| # | Name | X | n | p | q |
|---|------|---|---|---|---|
| A | 2-aminopropanoic acid | hydrogen | 0 | 1 | 0 |
| B | 2-amino-3-phenylpropanoic acid | phenyl | 0 | 1 | 0 |
| C | 2-amino-3-imidazolyl-propanoic acid | imidazolyl | 0 | 1 | 0 |
| D | 2-aminoacetic acid | not applicable | not applicable | | |
| E | 2-aminopentanedioic acid | —COOH | 2 | 1 | 0 |

While these substances are ineffective in preventing appearance of cold symptoms, they do not act as trigger substances and thus can be present in modest amounts as

Palatable oral dosage forms

Also in accordance with this invention, a pharmaceutically acceptable carrier can be combined with effective amounts of an effective agent according to this invention to provide a palatable oral dosage form for administering to a person in need of preventing appearance of cold symptoms. Accordingly, palatable oral dosage forms according to this invention comprise at least one pharmaceutically acceptable carrier and an effective amount of an effective agent according to this invention. Preferably the effective agent is an aminocarboxylic acid nutrient compound having formula (I). Particularly preferred effective agents are those listed in Table 1.

One preferred palatable oral dosage form according to this invention is a tablet. A particularly preferred tablet according to this invention comprises a high percentage of at least one aminocarboxylic acid nutrient compound having formula (I) and minor amounts of carrier material acting as binder for the tablet. Suitable binder materials include naturally occurring carbohydrates such as cellulose, starch, galactomannan, fructose, lactose, and sucrose; finely divided ingestible mineral substances such as calcium and magnesium carbonates, calcium and magnesium silicates, calcium and magnesium phosphates, alumina hydrates and hydrotalcite; waxy materials such as beeswax, stearin, stearates of calcium, magnesium, and aluminum, microcrystalline wax and paraffin, and mixtures thereof.

Another preferred palatable oral dosage form according to this invention is a capsule. Capsules have the advantage of delivering the effective agent directly to the alimentary canal without being tasted in the mouth. Suitable capsules are commercially available and are typically made of gelatin, but any sufficiently pure water soluble polymer can be used. Preferably the capsule is filled with the pure aminocarboxylic acid nutrient compound having formula (I); alternatively, suspensions of aminocarboxylic acid nutrient compound having formula (I) in a liquid carbohydrate such as corn syrup or honey, or in a lipid such as lecithin or canola oil can be encapsulated.

A further palatable oral dosage form according to this invention comprises an effective amount of an effective agent according to this invention in a liquid carrier such as a prepared soup or a fruit flavored drink, or in a solid concentrate ready to be converted to such liquid carrier by addition of water at the point of use.

Preferably the effective agent is an aminocarboxylic acid nutrient compound having formula (I). Particularly preferred effective agents are those listed in Table 1.

Suitable prepared soups include all flavors of canned and dehydrated soups, preferably in containers sized so as to deliver a single serving of soup containing an appropriate dose of the effective agent.

Suitable fruit flavored drinks include natural fruit juices such as pineapple juice, apple juice, grape juice, orange juice, grapefruit juice, cranberry juice, and mixtures thereof; reconstituted juices prepared from water and fruit juice concentrates, and fruit juice drinks containing water and at least 10% of natural fruit juice.

In oral dosage forms according to this invention, the proportions of carrier to effective agent can vary over a broad range in accordance with the kind of carrier selected and the strength desired. Thus the proportion of carrier can be as little as 0.1% by weight, as in a tablet, and as high as 85% or even more, as in a fruit flavored drink.

Tablets in accordance with this invention can be prepared, for example, from 750 milligrams of each of compounds #1, 3, 5, 6, or 7 of Table 1 and 5 milligrams each of stearin, magnesium stearate, and magnesium silicate.

Capsules in accordance with this invention can be prepared, for example, by filling elliptical capsules of 1.5 ml capacity with 500 milligrams of each of compounds #1, 2, 3, 4, 5, 6, or 7 of Table 1.

Fruit flavored drinks in accordance with this invention can be prepared, for example, from 3750 milligrams of each of compounds #1, 2, 3, 4, 5, 6, or 7 of Table 1 and 75 milliliters of commercially available apple-cranberry drink.

Pleasant tasting oral dosage forms

Also in accordance with this invention, a pharmaceutically acceptable carrier can be combined with effective amounts of an effective agent according to this invention and a flavorant to provide a pleasant tasting oral dosage form for administering to a person in need of preventing appearance of face pimples. Accordingly, pleasant tasting oral dosage forms according to this invention comprise at least one pharmaceutically acceptable carrier, an effective amount of an effective agent according to this invention, and a flavorant. Preferably the effective agent is an aminocarboxylic acid nutrient compound having formula (I). Particularly preferred effective agents are those listed in Table 1.

Preferred flavorants that can be used in a pleasant tasting oral dosage form according to this invention include herbs such as basil, cilantro, dill, oregano, tarragon, and thyme; spices such as cinnamon, clove, ginger, mace, and nutmeg, and essential oils such as oil of lemon, oil of orange, oil of peppermint, and oil of sassafras.

In a particularly preferred pleasant tasting oral dosage form according to this invention, there are present in amounts selected to complement the taste characteristics of each at least one first nutrient compound having the formula $$X-(CH_2)_n-CH(O)_qH-CH-COO^-$$
$$|$$
$$(NH_2^+)_pH$$

in which X is selected from the group consisting of $$-NH_2, \text{ and } -NH-C=NH$$
$$|$$
$$NH_2$$

, n is two, p is one and q is zero, and at least one second nutrient compound having the formula $$X-(CH_2)_n-CH(O)_qH-CH-COO-$$
$$|$$
$$(NH_2^+)_pH$$

in which X is selected from the group consisting of $-SH$, $-CONH_2$, $$-N(CH_3)_3^+, \quad -SCH_3, \text{ and}$$

$$-CO-NH-CH-CO-NHCH_2CO-OH,$$
$$|$$
$$CH_2SH$$

n is zero or one, and p and q are each zero or one, provided that p and q are not both zero and p is zero and q is one only when X is $-N(CH_3)_3^+$.

In such compositions, the taste characteristics of the first nutrient compound and the second nutrient compound interact in such a way as to produce an overall pleasant tasting composition.

Pleasant tasting tablets in accordance with this invention can be prepared, for example, from 750 milligrams of each of compounds #1, 3, 5, 6, or 7 of Table 1, 5 milligrams each of stearin, magnesium stearate, and magnesium silicate, and 10 milligrams of finely powdered cinnamon.

A pleasant tasting fruit flavored drink in accordance with this invention can be prepared, for example, by blending 4500 milligrams of each of compounds #1, 3, 5, 6, or 7 of Table 1, 110 milliliters of commercially available chilled grapefruit juice, and 5 drops oil of orange.

Pleasant tasting tablets containing a first nutrient compound and a second nutrient compound in accordance with this invention can be prepared, for example, from 500 milligrams of each of compounds #1, 2, 3, 5, 6, or 7 of Table 1, 250 milligrams of each of compounds #4 or 6 of Table 1, and 5 milligrams each of stearin, magnesium stearate, and magnesium silicate.

The following Examples are provided to illustrate the invention without intending to limit its scope, which is defined by the appended claims.

EXAMPLE 1

Conditions required to reproducibly trigger a running nose in a susceptible person were determined as follows:

A male volunteer subject known to be susceptible to attacks of running nose upon exposure to vapors of ammonia was seated in an enclosed room at varying distances from a 5½ inch diameter dish placed 3 feet above the floor and containing 40 milliliters of household ammonia (approximately 9% ammonia by weight in water). Trials were carried out on alternate days only to allow full recovery between trials. The time was noted from the start of exposure to the occurrence of a pronounced running nose, defined as having to blow clear 3 or more times in a 10 minute period and continuing for at least a six hour period. For each exposure distance, three trials were carried out, arranged in a random order.

| Trials | Distance of subject from source | Time to onset of running nose |
|---|---|---|
| a-1, a-2, a-3 | 12 feet | no reaction in one hour |
| b-1, b-2, b-3 | 8 feet | 15, 16, and 19 minutes |
| c-1, c-2, c-3 | 4 feet | 4, 4, and 3 minutes |
| d-1, d-2, d-3 | 2 feet | 2, 2, and 3 minutes |

The results show that exposure to ammonia vapors at a distance of 8 feet or less is clearly sufficient to reproducibly trigger a running nose in this individual.

EXAMPLES 2–3 and COMPARISON TRIALS 1–2

In each of the following trials, the same subject as in Example 1 was exposed to a dish of household ammonia at a distance of 4 feet. After the onset of running nose was noted, approximately eight minutes after exposure, there was administered a dose of a substance as noted below.

| Example no. | Substance | Dose | Time from administration to abatement of sneezing |
|---|---|---|---|
| 2 | Blend of substances from Table 1 | 2000 mg | 30 minutes |
| 4 | Blend of substances from Table 1 | 4000 mg | 20 minutes |
| Comparison 1 | none | | no effect in six hours |
| Comparison 2 | blend of substances from table 2 | 4000 mg | no effect in six hours |

The results show the blend of substances shown in Examples 2 and 3 was an effective agent according to this invention in relieving cold symptom such as running nose triggered by ammonia in accordance with a method of this invention. The results also show that compounds of Table 2 with structural similarity to those effective according to this invention but differing in the assignments of X and/or n in the formula were ineffective.

EXAMPLES 4–5 and COMPARISON TRIALS 3–4

In each of the following trials, there was administered a dose of a substance as noted below to the same subject as in Example 1, and after a waiting period of 30 minutes he was exposed to a dish of household ammonia at a distance of four feet. The following results were noted.

| Example no. | Substance | Dose | Results |
|---|---|---|---|
| 4 | Blend of substances from Table 1 | 2000 mg | no running nose within 6 hr |
| 5 | Blend of substances from Table 1 | 4000 mg | no running nose within 6 hr |
| Comparison 3 | none | | running nose after 4 min |
| Comparison 4 | blend of substances from table 2 | 4000 mg | running nose after 4 min |

The results show the blend of substances shown in Examples 5 and 6 was an effective agent according to this invention in preventing cold symptom such as running nose triggered by ammonia in accordance with a method of this invention. The results also show that compounds of Table 2 with structural similarity to those effective according to this invention but differing in the assignments of X and/or n in the formula were ineffective.

I claim:

1. An oral dosage form for relieving symptoms of the common cold in a person in need of such relief comprising a carrier and a quantity of at least one nutrient compound having the formula $$X-(CH_2)_n-CH(O)_qH-CH-COO^-$$
$$|$$
$$(NH_2^+)_pH$$

in which X is selected from the group consisting of —SH, —CONH$_2$,

—N(CH$_3$)$_3^+$, —SCH$_3$, —NH$_2$, —NH—C=NH and
$$|$$
$$NH_2$$

—CO—NH—CH—CO—NHCH$_2$CO—OH,
$$|$$
$$CH_2SH$$

n is zero, one, or two, and p and q are each zero or one, provided that p and q are not both zero and p is zero and q is one only when X is —N(CH$_3$)$_3$+.

2. An oral dosage form according to claim 1 in which the agent comprises a compound in which X is —SH and n is zero.

3. An oral dosage form according to claim 1 in which the agent comprises a compound in which X is —CONH$_2$ and n is one.

4. An oral dosage form according to claim 1 in which the agent comprises a compound in which X is —SCH$_3$ and n is one.

5. An oral dosage form according to claim 1 in which the agent comprises a compound in which X is —NH$_2$ and n is two.

6. An oral dosage form according to claim 1 in which the agent comprises a compound in which X is

—NH—C=NH
$$|$$
$$NH_2$$

and n is two.

7. An oral dosage form according to claim 1 in which the agent comprises a compound in which X is

—CO—NH—CH—CO—NHCH$_2$CO—OH
$$|$$
$$CH_2SH$$

and n is one.

8. An oral dosage form according to claim 1 selected from the group consisting of a tablet, a gelatin capsule, a soup, and a fruit flavored drink.

9. An oral dosage form according to claim 1 in which the proportions of carrier to agent are in the range of 4:1 to 1:4.

10. An oral dosage form according to claim 1, in which the carrier is at least one naturally occurring carbohydrate.

11. An oral dosage form according to claim 10, in which the carrier comprises lactose, sucrose, fructose, starch, or cellulose.

12. An oral dosage form according to claim 1, in which the carrier comprises at least one finely divided ingestible mineral substance.

13. An oral dosage form according to claim 12, in which the carrier comprises an alkaline earth metal carbonate or alkaline earth metal silicate.

14. An oral dosage form according to claim 1, in which the carrier comprises at least one lipid.

15. An oral dosage form according to claim 14, in which the carrier comprises lecithin or a fatty oil.

16. An oral dosage form according to claim 1 in which the quantity of agent is in the range of 200 to 20000 milligrams.

17. An oral dosage form according to claim 1, comprising an added flavorant.

18. A pleasant tasting oral dosage form according to claim 17, in which the flavorant is selected from the group consisting of herbs, spices, and essential oils.

19. An oral dosage form according to claim 1 comprising at least one first nutrient compound having the formula

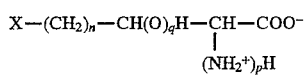

in which X is selected from the group consisting of

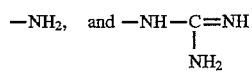

, n is two, p is one and q is zero, and at least one second nutrient compound having the formula

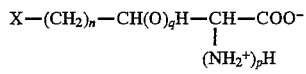

in which X is selected from the group consisting of —SH, —CONH$_2$,

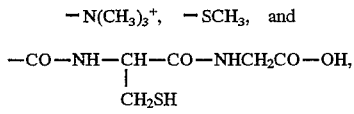

n is zero or one, and p and q are each zero or one, provided that p and q are not both zero and p is zero and q is one only when X is —N(CH$_3$)$_3$+.

in which the proportions of first nutrient compound and second nutrient compound are in the range from 4:1 to 1:4.

20. The method of determining the effectiveness of an agent for relieving symptoms of the common cold, comprising the steps of a) exposing a susceptible human subject to breathing vapors of a trigger substance reproducibly giving rise within a period of 30 minutes to a running nose in such subject lasting for at least 6 hours in the absence of treatment, b) administering to said subject being exposed to a trigger substance a predetermined quantity of the agent whose effectiveness is to be determined, c) measuring the time required for the running nose to be abated, and d) comparing the time required for the running nose to be abated with and without the administration of said agent, an effective agent being a nutrient compound having the formula

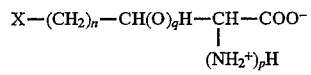

in which X is selected from the group consisting of —SH, —CONH$_2$,

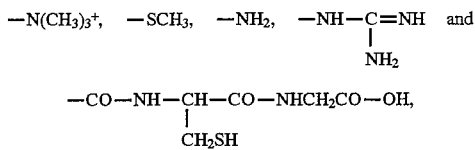

n is zero, one, or two, and p and q are each zero or one, provided that p and q are not both zero and p is zero and q is one only when X is —N(CH$_3$)$_3$+.

21. The method of claim 20 in which said trigger substance comprises ammonia water.

22. The method of claim 20 in which exposure to said trigger substance and administration of said agent are simultaneous.

23. The method of claim 20 in which said agent is administered prior to exposure to said trigger substance.

24. The method of claim 20 in which said agent is administered subsequent to exposure to said trigger substance.

25. The method of claim 21 in which the concentration of ammonia in the trigger substance is in the range from 1% to 35% by weight.

26. The method of relieving symptoms of the common cold in a person in need of such relief, comprising the administration to such person of a quantity of an agent determined to be effective by the method of claim 20.

27. The method of relieving symptoms of the common cold in a person in need of such prevention, comprising the administration to such person of a quantity of an agent determined to be effective by the method of claim 21.

28. The method of relieving symptoms of the common cold in a person in need of such relief, comprising the administration to such person of a quantity of at least one nutrient compound having the formula

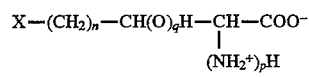

in which X is selected from the group consisting of —SH, —CONH$_2$,

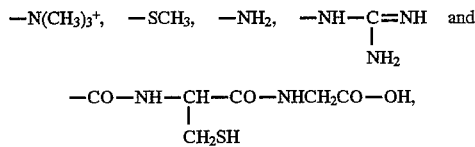

n is zero, one, or two, and p and q are each zero or one, provided that p and q are not both zero and p is zero and q is one only when X is —N(CH$_3$)$_3$+.

29. The method of claim 28 in which X is —SH and n is zero.

30. The method of claim 28 in which X is —CONH$_2$ and n is one.

31. The method of claim 28 in which X is —SCH$_3$ and n is one.
32. The method of claim 28 in which X is —NH$_2$ and n is two.
33. The method of claim 28 in which X is
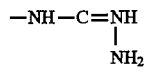
and n is two.
34. The method of claim 28 in which X is
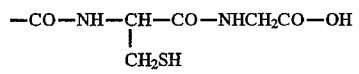
and n is one.
35. The method of claim 28 in which X is —N(CH$_3$)$_3$+, n is zero, p is zero, and q is one.
* * * * *